United States Patent [19]
Whitaker

[11] Patent Number: 5,520,168
[45] Date of Patent: May 28, 1996

[54] GAS FLOW UNITS

[75] Inventor: Keith Whitaker, Keighley, England

[73] Assignee: The BOC Group plc, Windlesham, England

[21] Appl. No.: 219,333

[22] Filed: Mar. 28, 1994

[30] Foreign Application Priority Data

Apr. 2, 1993 [GB] United Kingdom ............... 9307022

[51] Int. Cl.⁶ ............................................. A61M 16/00
[52] U.S. Cl. .................. 128/202.22; 128/203.12; 128/203.25
[58] Field of Search .............. 128/200.14, 203.12, 128/203.24, 203.25, 202.22

[56] References Cited

U.S. PATENT DOCUMENTS

| | | | |
|---|---|---|---|
| 4,307,718 | 12/1981 | Schreiber | 128/200.14 |
| 4,308,865 | 1/1982 | Hay | 128/200.14 |
| 4,346,701 | 8/1982 | Richards | 128/200.14 |
| 4,351,327 | 9/1982 | Rinne et al. | 128/200.14 |

FOREIGN PATENT DOCUMENTS

| | | |
|---|---|---|
| 1385670 | 2/1975 | United Kingdom . |
| 2052271 | 1/1981 | United Kingdom . |

*Primary Examiner*—Aaron J. Lewis
*Attorney, Agent, or Firm*—Roger M. Rathbun; R. Hain Swope; Larry R. Cassett

[57] ABSTRACT

An anaesthetic vaporizer includes a concentration dial for controlling the concentration of anaesthetic leaving the vaporizer. The vaporizer is adapted to be mounted on a back bar of an anaesthesia machine. An exclusion pin is mounted adjacent the back bar and forms part of an interlock system for preventing rotation of the concentration dial when a second vaporizer is also mounted on the back bar and is dispensing anaesthetic vapor. A button assembly is mounted on the concentration dial and must be depressed before the concentration dial can be rotated. The button assembly incorporates an overload device which, if excessive force is applied to the button assembly in order to override the effect of the exclusion pin will render the button assembly inoperative.

2 Claims, 5 Drawing Sheets

GAS FLOW UNITS

BACKGROUND OF THE INVENTION

The present invention relates to gas flow units which are adapted to be mounted on gas administration machines. More particularly, the present invention relates to anaesthetic vaporisers which are adapted to be mounted on anaesthesia machines for the administration of gaseous anaesthetics or analgesics or other "medical" gases or gas mixtures, such as oxygen or air.

For the avoidance of doubt throughout this specification the term "anaesthetic" is intended to embrace gaseous anaesthetics, gaseous analgesics or other "medical" gases or gas mixtures such as oxygen or air.

Conventionally, anaesthesia machines frequently incorporate two or more separate anaesthetic vaporisers. Each vaporiser is arranged to dispense a specific amount of a particular anaesthetic, for example, halothane, enflurane, methoxyflurane etc., in a patient's breathing circuit or gas line.

In United Kingdom patent specification No. 1385670 there is described an anaesthesia machine on which one or more vaporisers can be mounted in a removable, plug-in fashion. A plug-in system of this nature simplifies the installation and removal of the vaporisers from the machine thereby facilitating maintenance and cleaning of the vaporisers as well as replacing a vaporiser should it fail during operation. Furthermore, this system is of great value to the anaesthetist in allowing him to change vaporisers both easily and quickly.

In United Kingdom patent specification No. 2052271, there is described an arrangement whereby two or more vaporisers are mounted on a back bar of an anaesthesia machine. Each vaporiser has an interlock system which includes at least one pin extendible outwardly from the vaporiser on manipulation of the control means for the vaporiser to its operating position to prevent the control means of a similar adjacent vaporiser mounted on the anaesthesia machine from being manipulated to its operating position.

However, if the vaporiser control means were to be subjected to misuse by the application of excessive force thereto it is possible that the interlock system could be overridden.

If this were to occur, it could mean that two or more vaporisers on the same anaesthesia machine could be operated at the same time thereby administering their respective anaesthetics to a patient.

SUMMARY OF THE INVENTION

It is an aim of the present invention to provide a gas flow unit such as an anaesthetic vaporiser with an overload device which prevents or substantially reduces any possibility for the interlock system to be misused.

According to one aspect of the present invention a gas flow unit comprises means including a concentration dial for controlling the concentration of gas leaving the unit, button means movable between a first position in which the concentration dial is immobilised in an "off" position and a second position in which the concentration dial is released to move from the "off" position, said button means including an overload device which under normal working conditions is movable with the button means from the first to the second position to release the concentration dial but when an overload is applied to the button means will render the button means inoperative.

According to a further aspect of the present invention an anaesthetic vaporiser comprises means for controlling the concentration of anaesthetic agent leaving the vaporiser including a concentration dial movable between an "off" position and a fully "on" position, the vaporiser being adapted to be mounted on an anaesthesia machine which includes an interlock mechanism which cooperates with interlock means on the vaporiser for preventing movement of the concentration dial from its "off" position when a second vaporiser is mounted on the anaesthesia machine and the second vaporiser's concentration dial has been moved from its "off" position towards its fully "on" position, and button means movable between a first position in which the concentration dial is prevented from movement from its "off" position to a second position in which the concentration dial is free to move from said "off" position said button means including an overload device which under normal working conditions is movable with the button means from the first to the second position to release the concentration dial but when an overload is applied will render the button means inoperative.

BRIEF DESCRIPTION OF THE DRAWINGS

An embodiment of the invention will now be described by way of example, reference being made to the Figures of the accompanying diagrammatic drawings in which.

DETAILED DESCRIPTION OF THE PREFERRED EMBODIMENT

Figure 1:
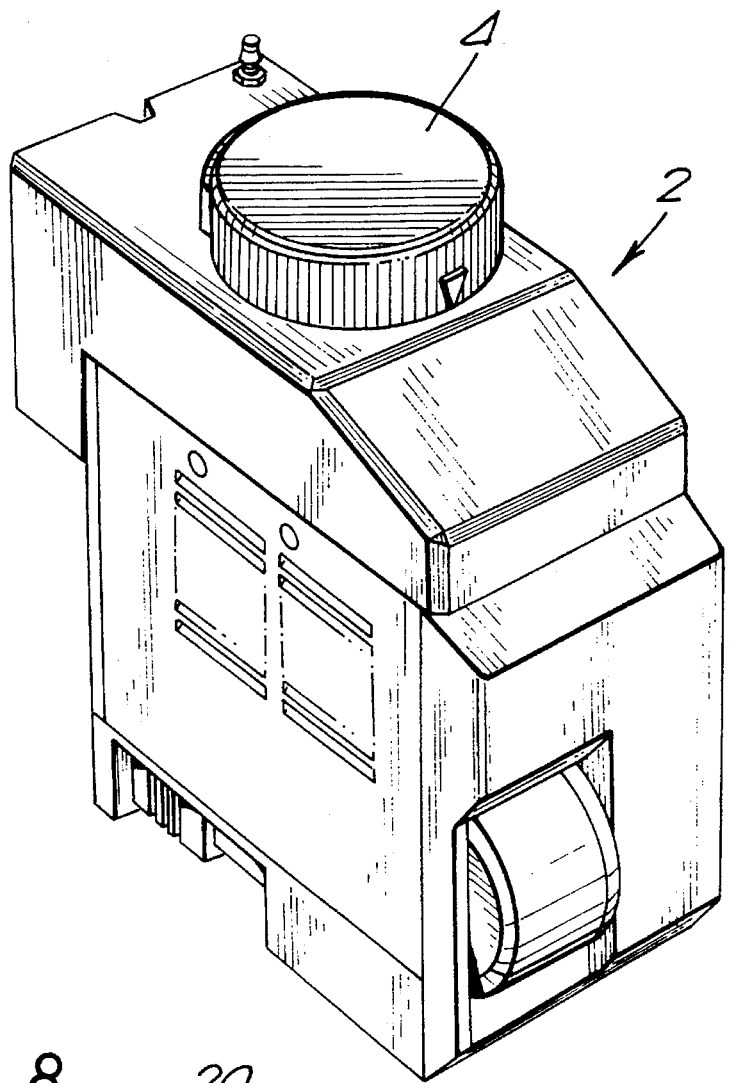
FIG. 1 is a perspective view of an anaesthetic vaporiser.
Figure 2:
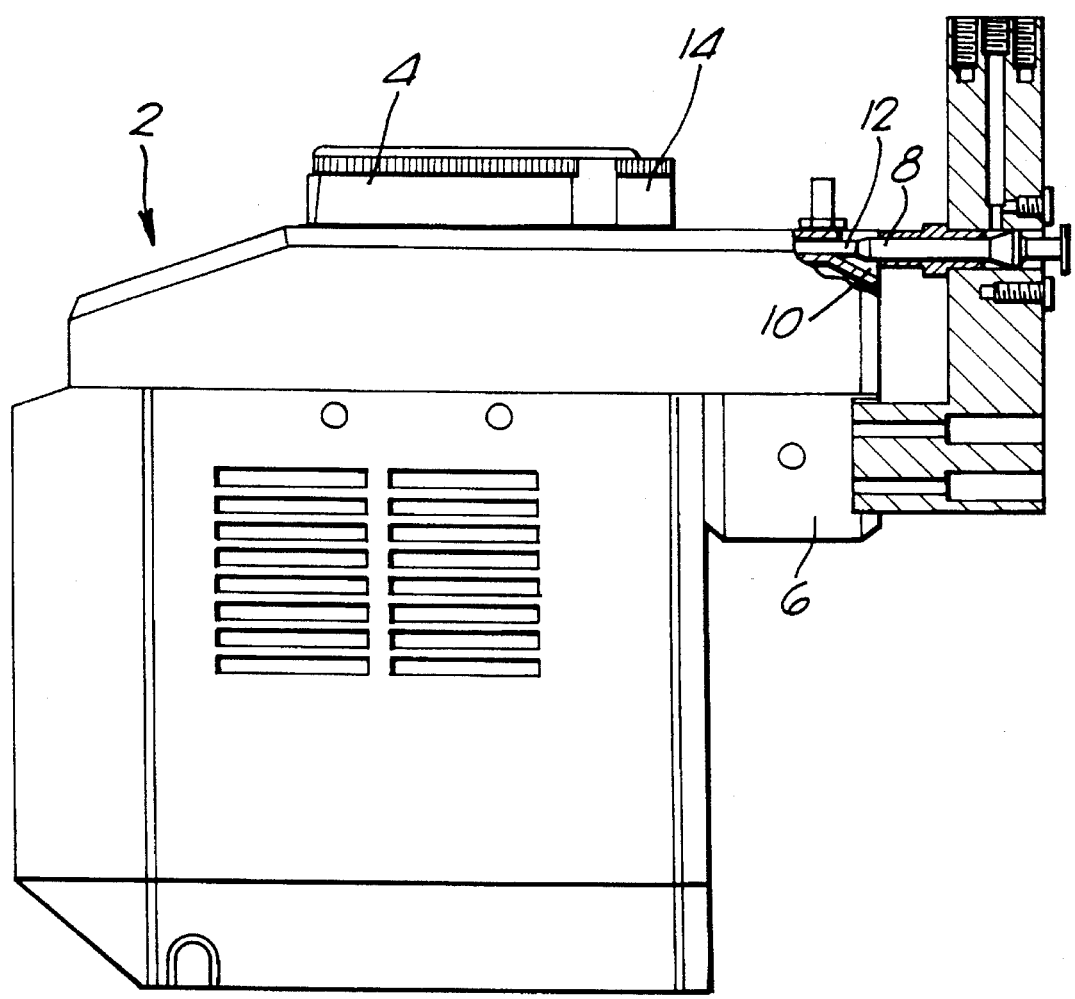
FIG. 2 is a side elevation of the anaesthetic vaporiser of FIG. 1 mounted on the back bar of an anaesthesia machine.

Referring now to FIGS. 1 and 2, there is shown an anaesthetic vaporiser 2 of known construction save for the overload device to be described. The vaporiser 2 includes a concentration dial 4 linked to a rotary plate or other suitable form of control valve located within the body of the vaporiser. The concentration of the anaesthetic agent provided by the vaporiser 2 is determined by the setting of the concentration dial 4 in a manner known in the art. As illustrated in FIG. 2 the vaporiser 2 can be installed in a removable plug-in fashion or bolted on a back bar 6 of an anaesthesia machine again in a manner known in the art. Mounted adjacent the back bar is an exclusion pin 8 forming part of an interlock system which is intended to prevent the rotary movement of the concentration dial 4 when a second vaporiser (not shown) also mounted on the back bar 6 is dispensing anaesthetic vapour.

The interlock system will not be described in detail except to say that when said second vaporiser is being used, that is its concentration dial has been moved from its "off" position, the exclusion pin 8 will extend into a recess 10 formed in the body of the vaporiser 2 thereby preventing the extension of an actuating pin 12 forming part of the vaporiser 2 out from the vaporiser 2.

Slidably mounted on the concentration dial 4 is a button assembly 14.

Figure 3:
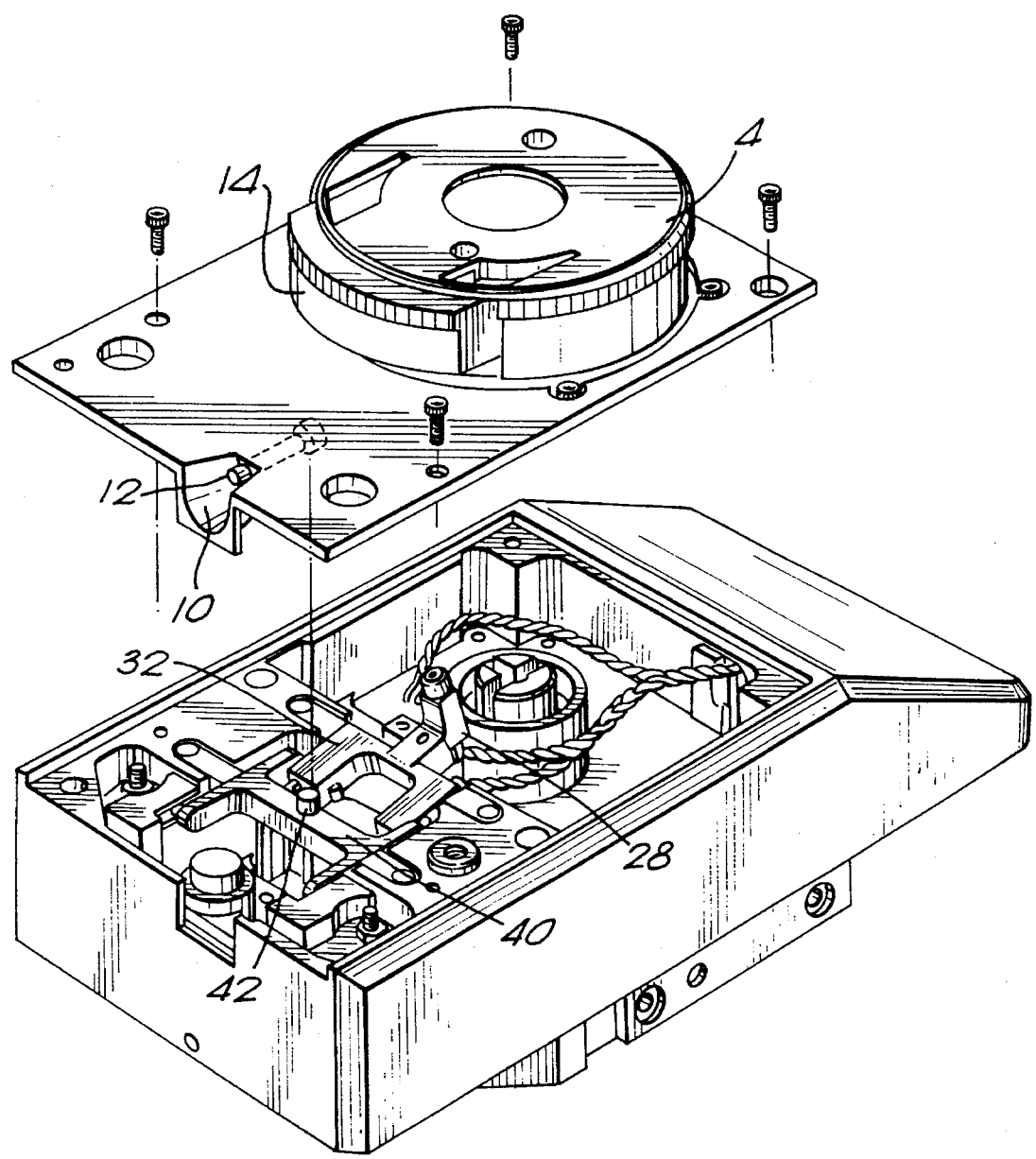
FIG. 3 is a perspective, exploded view of an upper portion of the anaesthetic vaporiser of FIG. 1.
Figure 4:
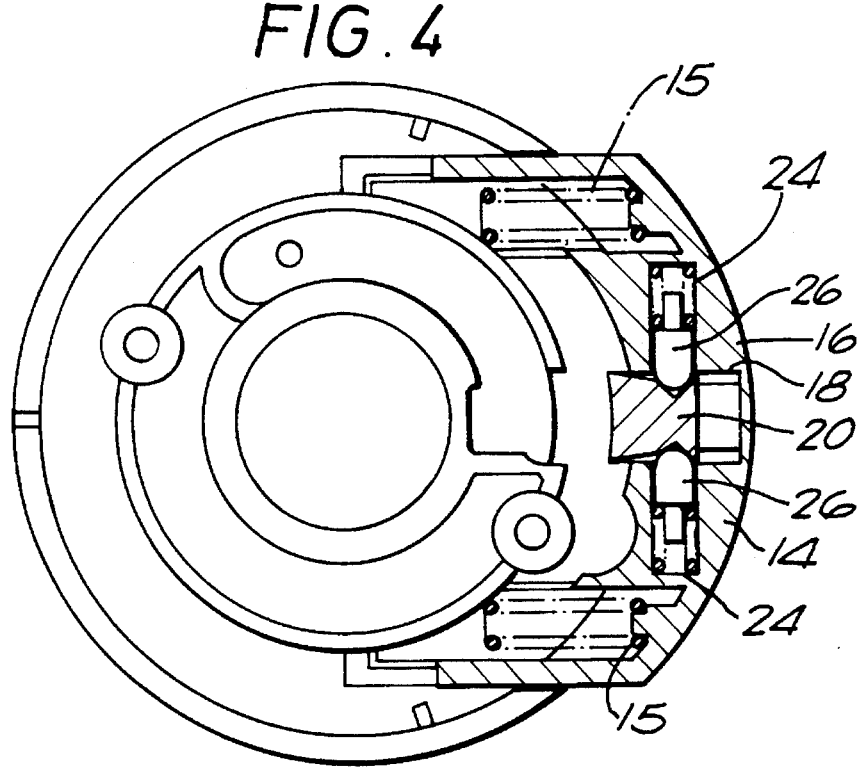
FIGS. 4 and 5 are plan views partly in cross-section illustrating a concentration dial of the vaporiser of FIG. 1 together with a button illustrated in a normal working position and a misuse or overload position respectively.
Figure 5:
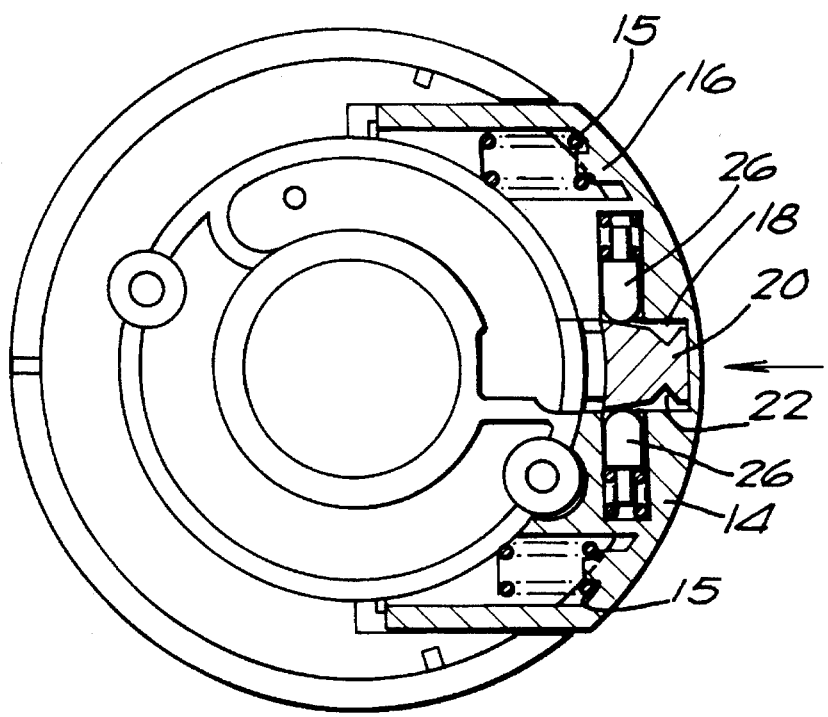

Referring in particular to FIGS. 3, 4 and 5, the button assembly 14 includes a housing 16 located at one side of the concentration dial 4. The button assembly 14 is urged by springs 15 towards a first position away from the concentration dial 4 in which first position of the button assembly 14 the concentration dial 4 is immobilised in its "off" position; and is movable towards a second position against the action of the springs 15 in which second position of the button assembly 14 the concentration dial 4 is released to move from its "off" position. The housing 16 incorporates an overload device and is formed with a central (as shown) bore 18 which accommodates an actuator 20. The actuator 20 is movable longitudinally within the bore 18 and is formed with grooves 22 in its outer surfaces.

Also formed in the housing 16 on each side of the bore 18 is a cavity 24. Each cavity 24 contains a spring-loaded plunger 26 which as illustrated in FIG. 4 under normal working conditions of the vaporiser 2 will latch into the grooves 22 of the actuator 20.

Figure 8:
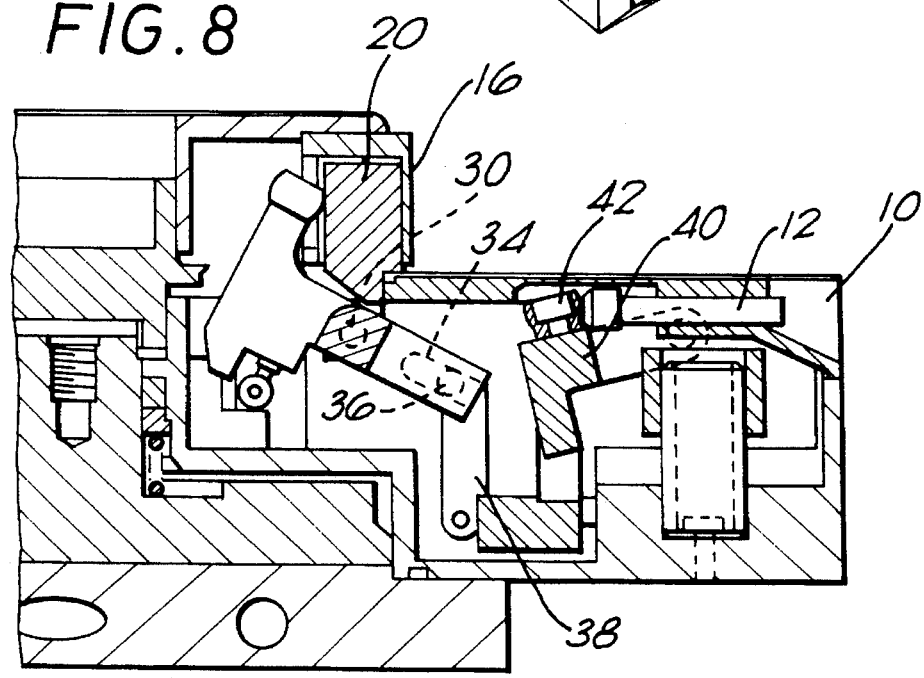
FIG. 8 is a view similar to FIGS. 6 and 7 with the vaporiser in a misuse or overload position.
Figure 6:
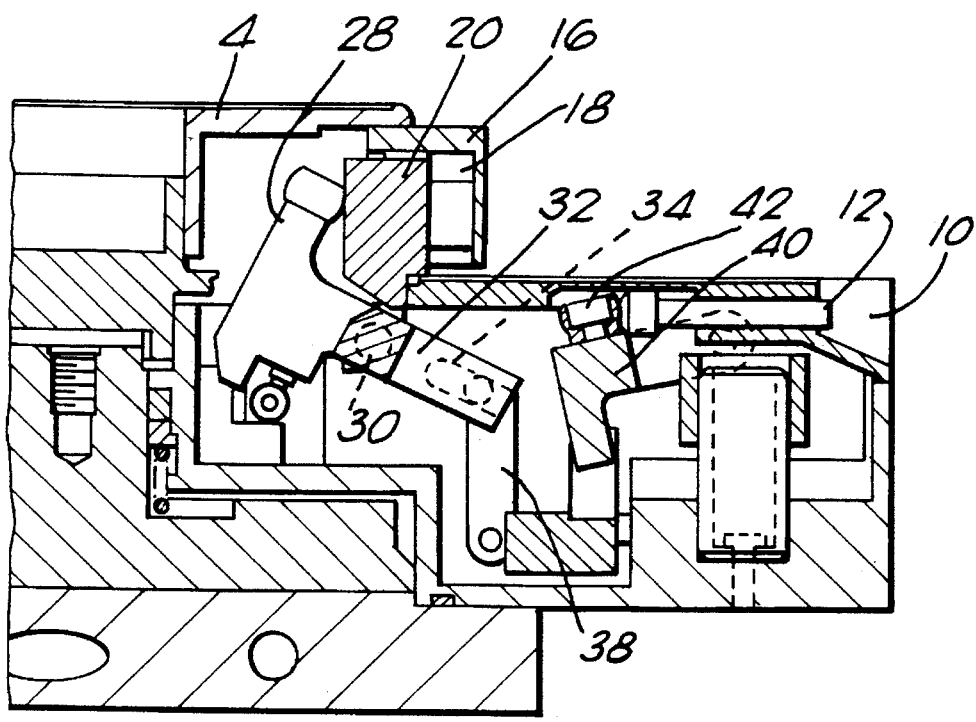
FIG. 6 is a side elevation partly in cross-section of a detail of the anaesthetic vaporiser of FIG. 1 with the vaporiser in an "off" position.
Figure 7:
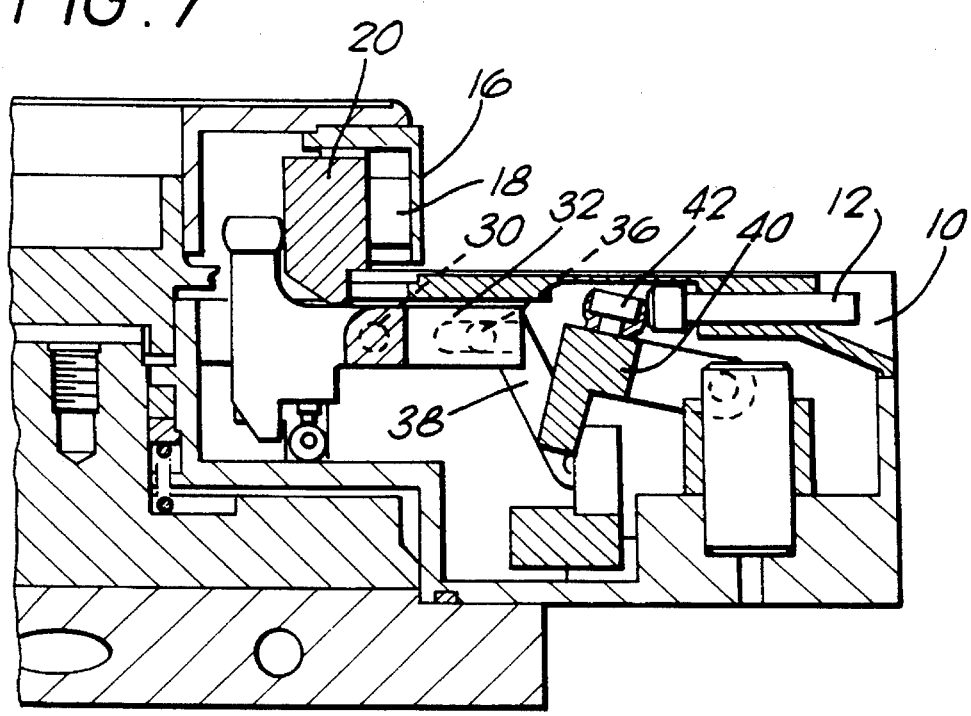
FIG. 7 is a view similar to FIG. 6 but with the vaporiser in an "on" position.

Referring also to FIGS. 6, 7 and 8 the forward end of the actuator 20 is in contact with a member 28 pivotally mounted within the vaporiser 2 by means of pin 30. The member 28 has a bifurcated tail part 32 including a slot 34 in which is engaged a link pin 36 connected to a pivotal link member 38. The link member 38 is pivotally connected to a further member 40 having a boss 42 which is positioned to engage the actuator pin 12 the distal end of which is located within the recess 10 of the vaporiser 2.

Referring in particular to FIGS. 4 and 6, when the vaporiser 2 is mounted on back bar 6 but the vaporiser 2 is in its off position, that is, it is not dispensing anaesthetic vapour the button assembly 14 will be positioned relative to the concentration dial 4 as shown in FIGS. 4 and 6. In this position, the spring-loaded plungers 26 will engage the grooves 22 in the actuator 20; the button assembly 14 will extend from the concentration dial 4 and the various members and linkages 28, 30, 32, 36, 38, 40 anb 42 will be positioned such that the actuator pin 12 is in its retracted position as shown in FIG. 6.

In operation, when it is desired that the vaporiser 2 shall commence to administer anaesthetic vapour the button assembly 14 will be depressed (see FIG. 7) the actuator 20 will move with the button assembly 14 and will engage the member 28 whose movement will be translated by the transmission linkages and pivots such that the actuator pin 12 will extend farther out from the vaporiser 2 as illustrated in FIG. 7. In this position the actuator pin 12 will engage the exclusion pin 8 located adjacent to the back bar as illustrated in FIG. 2 so that the operation of a concentration dial on a similar vaporiser located on the back bar will be prevented.

The above operation will be carried out under the normal working conditions of the vaporiser 2.

In the event that excessive force is applied to the button assembly 14 in order to override the effect of the exclusion pin 8, i.e. while another vaporiser is in use, a load will be applied to the button assembly 14 by the hand of the operator. As the force increases the holding force of the spring-loaded plungers 26 is exceeded and the housing 16 will move leaving the actuator 20 stationary (see FIGS. 5 and 8). Although the button assembly 14 is depressed the operator will be unable to turn the concentration dial 4 and an audible click will indicate to the operator that the overload device has been activated. Thus it will be substantially impossible for the button assembly 14 to be misused to such an extent that the interlock system of the vaporisers and the anaesthesia machine can be over-ridden.

The release of the button assembly 14 will automatically allow the spring-loaded plungers 26 to return to sit in the grooves 22 of the actuator 20 such that the actuator 20 will return to its normal working position within the button assembly 14.

Although reference has been made in the above described embodiment to an anaesthetic vaporiser the overload device could equally be applied to other "gas-flow units" capable of being mounted on a gas-administration machine, for example, flow meters, gas mixers, volume meters, ventilators, pressure gauges and adsorbers.

I claim:

1. A gas flow unit comprising means including a concentration dial for controlling the concentration of gas leaving the unit, button means movable between a first position in which the concentration dial is immobilized in an off position and a second position in which the concentration dial is released to move from the off position, said button means including an overload device comprising an actuator which is located within a bore of a housing forming part of the button means and is maintained against movement relative to the housing by at least one spring loaded plunger and which is, under normal conditions, movable with the button means from the first to the second position to release the concentration dial but when an overload is applied to the button means, the holding force of the spring loaded plunger will be overcome allowing the button means to move relative to the actuator within said bore and said actuator does not move, whereby moving said button means from the first to the second position will not release the concentration dial for movement from the off position.

2. A gas flow unit as claimed in claim 1, in which the actuator includes grooves in which are located under normal working conditions the ends of two oppositely opposed spring loaded plungers.

\* \* \* \* \*